(12) United States Patent
Townsend et al.

(10) Patent No.: US 7,735,501 B2
(45) Date of Patent: Jun. 15, 2010

(54) MOBILITY ASSISTANCE APPARATUS AND METHOD

(75) Inventors: Barry W. Townsend, Bakersfield, CA (US); Byron K. Claudino, Bakersfield, CA (US)

(73) Assignee: Bioquest Prosthetics LLC, Bakersfield, CA (US)

( * ) Notice: Subject to any disclaimer, the term of this patent is extended or adjusted under 35 U.S.C. 154(b) by 1706 days.

(21) Appl. No.: 10/915,724

(22) Filed: Aug. 11, 2004

(65) Prior Publication Data

US 2005/0016572 A1 Jan. 27, 2005

Related U.S. Application Data

(63) Continuation-in-part of application No. 10/814,260, filed on Apr. 1, 2004, now Pat. No. 7,611,543, and a continuation-in-part of application No. 10/814,155, filed on Apr. 1, 2004, now Pat. No. 7,410,503, which is a continuation-in-part of application No. 10/263,795, filed on Oct. 4, 2002, now Pat. No. 7,226,485, which is a continuation of application No. 09/820,895, filed on Mar. 30, 2001, now Pat. No. 6,562,075.

(51) Int. Cl.
*A61H 3/02* (2006.01)
*A61F 2/66* (2006.01)

(52) U.S. Cl. .............................. 135/71; 135/66; 135/82; 135/84; 623/38; 623/55

(58) Field of Classification Search ............. 135/65–66, 135/68, 69–71, 72, 77, 82, 84, 73; 623/32, 623/38, 52–5, 583, 27, 29, 47, 50, 53, 55
See application file for complete search history.

(56) References Cited

U.S. PATENT DOCUMENTS 127,028 A 5/1872 Crandall (Continued)

FOREIGN PATENT DOCUMENTS

DE 299 20 434 U1 4/2000

(Continued)

OTHER PUBLICATIONS

Canadian Office Action dated Feb. 16, 2009; Application No. 2,446,768; 3 pages; Owner: Barry W. Townsend, et al.; Title: Prosthetic Foot With Tunable Performance.

(Continued)

*Primary Examiner*—Winnie Yip
(74) *Attorney, Agent, or Firm*—Antonelli, Terry, Stout & Kraus, LLP.

(57) ABSTRACT

A mobility assistance apparatus and a method for improving the mobility of a person using a walking aid, such as a cane, crutch, or walker, involve use of a device for ground engagement with ambulating using the walking aid. In a preferred example the device is a resilient lower extremity prosthesis that is capable of storing and releasing energy to generate propulsive force to aid mobility. The prosthesis has a foot, ankle and shank. The shank has a lower portion that is anterior facing convexly curved for generating forward propulsion with ambulating to aid mobility.

24 Claims, 12 Drawing Sheets

U.S. PATENT DOCUMENTS

| | | | |
|---|---|---|---|
| 241,226 A * | 5/1881 | Landis | 623/28 |
| 267,680 A | 11/1882 | Crandall | |
| 1,254,061 A | 1/1918 | Mueller | |
| 1,277,009 A | 8/1918 | Weldon | |
| 2,453,969 A | 11/1948 | Carter | |
| 3,040,757 A | 6/1962 | Smith | |
| 3,738,674 A * | 6/1973 | Pauls | 280/816 |
| 3,948,535 A * | 4/1976 | Negi | 280/816 |
| 4,098,283 A | 7/1978 | Tritle, Jr. | |
| 4,237,915 A | 12/1980 | Zabielski et al. | |
| 4,411,284 A | 10/1983 | Opitz | |
| 4,493,334 A * | 1/1985 | Semanchik et al. | 135/75 |
| 4,708,154 A | 11/1987 | Edwards | |
| 4,884,587 A * | 12/1989 | Mungons | 135/65 |
| 4,899,771 A | 2/1990 | Wilkinson | |
| 4,911,724 A | 3/1990 | Fikes | |
| 5,116,384 A | 5/1992 | Wilson et al. | |
| 5,139,525 A * | 8/1992 | Kristinsson | 623/55 |
| 5,167,746 A | 12/1992 | Sheenan | |
| 5,224,506 A | 7/1993 | Allen et al. | |
| 5,301,704 A * | 4/1994 | Brown | 135/78 |
| 5,331,989 A | 7/1994 | Stephens | |
| 5,335,683 A * | 8/1994 | Ledley | 135/84 |
| 5,353,825 A | 10/1994 | Davis | |
| 5,387,246 A | 2/1995 | Phillips | |
| 5,409,029 A | 4/1995 | Davis | |
| 5,458,656 A | 10/1995 | Phillips | |
| 5,465,745 A | 11/1995 | Davis | |
| 5,509,936 A | 4/1996 | Rappoport et al. | |
| 5,651,792 A | 7/1997 | Telikicherla | |
| 5,653,768 A | 8/1997 | Kania | |
| 5,766,265 A * | 6/1998 | Phillips | 623/52 |
| 5,829,463 A | 11/1998 | Galan | |
| 5,897,594 A * | 4/1999 | Martin et al. | 623/53 |
| 5,954,075 A * | 9/1999 | Gilmour | 135/84 |
| 6,085,766 A | 7/2000 | Geary | |
| 6,155,998 A | 12/2000 | Gilmour | |
| 6,361,515 B1 | 3/2002 | Gilmour | |
| 6,494,919 B1 | 12/2002 | Matthews | |
| 6,514,293 B1 | 2/2003 | Jang et al. | |
| 6,562,075 B2 | 5/2003 | Townsend et al. | |
| 6,634,608 B2 | 10/2003 | Jacobowitz | |
| 7,360,547 B2 * | 4/2008 | Carlson | 135/66 |
| 2001/0001959 A1 | 5/2001 | Iwasa | |
| 2001/0027802 A1 | 10/2001 | McGrath | |
| 2002/0087216 A1 | 7/2002 | Atkinson et al. | |
| 2002/0133237 A1 | 9/2002 | Christesen | |
| 2002/0144430 A1 | 10/2002 | Schmid | |
| 2002/0144723 A1 | 10/2002 | Zulla et al. | |
| 2003/0009238 A1 | 1/2003 | Whayne | |
| 2003/0028256 A1 | 2/2003 | Townsend et al. | |
| 2003/0045944 A1 | 3/2003 | Mosler et al. | |
| 2003/0120354 A1 | 6/2003 | Doddroe et al. | |
| 2005/0016572 A1 | 1/2005 | Townsend et al. | |

FOREIGN PATENT DOCUMENTS

| | | | |
|---|---|---|---|
| FR | 2734151 | | 11/1996 |
| GB | 2425253 A | * | 10/2006 |
| JP | 08206165 A | * | 8/1996 |
| JP | 2003153716 A | * | 5/2003 |
| WO | WO 99/52476 | | 10/1999 |

OTHER PUBLICATIONS

European Office Action dated Apr. 3, 2009; Application No. 02 733 905.0-2310; 4 pages; Applicant: Barry W. Townsend, et al.

International Search Report; PCT/US05/11304 ; Filed : Apr. 1, 2005.

International Search Report; PCT/US05/11291; Filed: Apr. 1, 2005.

International Search Report; International Filing Date: Apr. 26, 2006; International Application No. PCT/US06/15627; Report mailed Sep. 24, 2007.

Written Opinion of the International Search Authority; International Filing date: Apr. 26, 2006; International Application No. PCT/US06/15627.

Canadian Office Action; Application No. 2,519,683; 2 pages; Owner: Barry w. Townsend, et al.; Title: Mobility Assistance Apparatus and Method.

* cited by examiner

MOBILITY ASSISTANCE APPARATUS AND METHOD

RELATED APPLICATIONS

This application is a continuation in part of application Ser. Nos. 10/814,260 now U.S. Pat. No. 7,611,543 and Ser. No. 10/814,155 (now U.S. Pat. No. 7,410,503 issued Aug. 12, 2008) each filed Apr. 1, 2004, which in turn are continuation in part applications of Ser. No. 10/263,795 filed Oct. 4, 2002, (now U.S. Pat. No. 7,226,485 issued Jun. 5, 2007), which is a continuation of application Ser. No. 09/820,895 filed Mar. 30, 2001, now U.S. Pat. No. 6,562,075 issued May 13, 2003. Applicants claim priority of these prior applications under 35 U.S.C. §120. The disclosures of the prior applications are hereby incorporated by reference.

The application is also related to the following U.S. applications:
 Ser. No. 10/408,107 filed Apr. 8, 2003, now U.S. Pat. No. 7,364,593 issued Apr. 29, 2008;
 Ser. No. 10/473,682 filed Mar. 29, 2002, now U.S. Pat. No. 7,507,259 issued Mar. 24, 2009;
 Ser. No. 10/473,465 filed Mar. 29, 2002, now U.S. Pat. No. 7,429,272 issued Sep. 30, 2008;
 Ser. No. 10/473,680 filed Mar. 29, 2002, now U.S. Pat. No. 7,211,115 issued May 1, 2007;

and the application is related to the following international applications designating the U.S.:
 PCT/US02/30471 filed Sep. 26, 2002;
 PCT/US03/09506 filed Mar. 31, 2003.

The disclosures of these additional related applications are also hereby incorporated by reference.

TECHNICAL FIELD

The present invention is directed to an improved mobility assistance apparatus and a method of improving the mobility of a person using a walking aid such as a cane, crutch or walker.

BACKGROUND

For over a century crutches and canes have remained virtually unchanged. Modifications to the crutch or cane itself have generally focused on ergonomic improvements in the physical structure versus functional improvements to mobility. As such, modern ambulatory aids continue to suffer from many of the same functional limitations that plagued their predecessors.

An example of an early crutch, in U.S. Pat. No. 127,028 issued May 21, 1872, involves the use of a round rubber tip made of respective layers of rubber and canvas, each exposed at the tip, to prevent the crutch from slipping on a wet surface. The use of a passive curved rocker provided at the lower end of the crutch to increase the progression or ground covered with use of the crutch is taught by U.S. Pat. No. 267,680 issued Nov. 21, 1882. A pneumatic cushion is used to form a curved rocker or bearer at the tip of the crutch in the patent to Mueller, U.S. Pat. No. 1,254,061 issued Jan. 22, 1918. The U.S. Pat. No. 1,277,009 to Weldon, issued Aug. 27, 1918, teaches the use of curved segmental base pieces at the tip of the crutches for ground engagement.

More recently, examples of annular crutch tips with features to resist slipping when engaged with the ground are shown by U.S. Pat. Nos.: 3,040,757; 4,098,283; 4,411,284; 4,237,915 and 4,708,154. A radial crutch tip assembly with a base bottom surface and a resilient boot having a shape of a rocker is disclosed by Davis in each of U.S. Pat. Nos. 5,353,825; 5,409,029 and 5,465,745.

In other examples of walking aids, Wilkinson, U.S. Pat. No. 4,899,771, provides a foot member for the walking aid which is curved upwardly at its front and back ends to permit limited rolling of the foot member when used with a cane or crutch during a walking procedure. Similarly, Stephens discloses in U.S. Pat. No. 5,331,989 curving the front, rear and inner sides of the foot member of a walking aid to permit limited rolling of the crutch tip laterally as well as forward and backward.

Galan, in U.S. Pat. No. 5,829,463 provides the crutch tip with a heel portion or extension extending rearwardly from the tip at an upward angle. The heel portion is used to prevent slipping when the user is rising from a seated position. Semanchik et al. disclose in U.S. Pat. No. 4,493,334 a walking aid having a foot pad shaped with a curved sole to simulate an anatomical foot for achieving a rocking movement in use by imitating the phases of a normal gait, i.e. heel strike, foot flat and toe off. A published U.S. patent application, U.S. Ser. No. 2001/0027802 A1 to McGrath, is directed to a walking aid comprising a shaft and a foot assembly, in which the foot assembly includes in combination a sleeve member and a foot member adapted for relative axial sliding movement and including resilient movement-restraint means for alleviating problems from shock loading transferred up the walking aid to the user's hand, wrist, arm and shoulder.

One of the single largest deficiencies of conventional walking assistance devices is the excessive amount of energy needed to stabilize the walking system (the device and the user's body) with the ground, and to efficiently move the user's body through space. In fact, a crutch user expends as much as 2.5 times more energy to move his/her body mass, in space, as compared to an able bodied person. Furthermore, the lack of sufficient surface area at the ground engaging surface of a walking assistance device engenders other dangers such slippage on uneven or slick surfaces. While improvements have been made with respect to the surface area at the point of contact for walking assistance devices, these improvements have been one-dimensional due to the limitations of the designs. It has been found by Applicants that the principal limitation to even the most progressive crutch or cane tip, with respect to surface area and/or surface textures, is the inability of these devices to stabilize the walking system while simultaneously translating the vertical forces associated with crutch/cane ambulation into forward propulsion and mobility. There is a need for an improved mobility assistance apparatus capable of stabilizing the walking system while lessening the user's necessary energy expenditure and discomfort associated therewith.

SUMMARY OF INVENTION

An object of the present invention is to address the aforementioned need. To this end, the present invention is an improved mobility assistance apparatus and a method of improving the mobility of a person using a walking aid, which lessen the user's necessary energy expenditure and discomfort associated therewith by translating the vertical forces associated with ambulating using a walking aid into forward propulsion and mobility while at the same time stabilizing the walking system. In accordance with the invention, a method of improving the mobility of a person using a walking aid comprises providing a device having a dynamic response characteristic to forces associated with ambulating using a walking aid which generates forward propulsion to aid mobility, and connecting the device to a lower portion of a walking aid for ground engagement with ambulating using the walking aid. In accordance with a preferred embodiment of the invention, the device is a lower extremity prosthesis. In an example embodiment, the prosthesis includes a resilient foot, ankle and shank. An upper portion of the shank is connected to a lower end of the walking aid.

A mobility assistance apparatus of the invention comprises a support member capable of bearing vertical forces during use of the support member as a walking aid, and a device connected to a lower portion of the support member for a ground engagement, the device having a dynamic response characteristic to forces associated with ambulating using the support member as a walking aid which generates forward propulsion to aid mobility. As noted above, the device in an example embodiment is a resilient prosthesis including a foot, ankle and shank connected to a lower portion of the support member for ground engagement. The resilient prosthesis stores energy during force loading and releases stored energy during force unloading to generate propulsive force.

The walking aid is preferably selected from the group consisting of a crutch, a cane, and a walker. The device connected to a lower portion of the walking aid, the resilient prosthesis in the example embodiment, is capable of sagittal and transverse plane motion in response to forces associated with ambulating using the walking aid. This ensures that the bottom, ground engaging surface of the device/resilient prosthesis remains parallel to the ground, maintaining maximum contact and traction throughout the ambulatory cycle.

These and other objects, features and advantages of the present invention will be more apparent from a consideration of the following detailed description of disclosed example embodiments of the invention and the accompanying drawings.

DETAILED DESCRIPTION OF EMBODIMENTS

Figure 1:
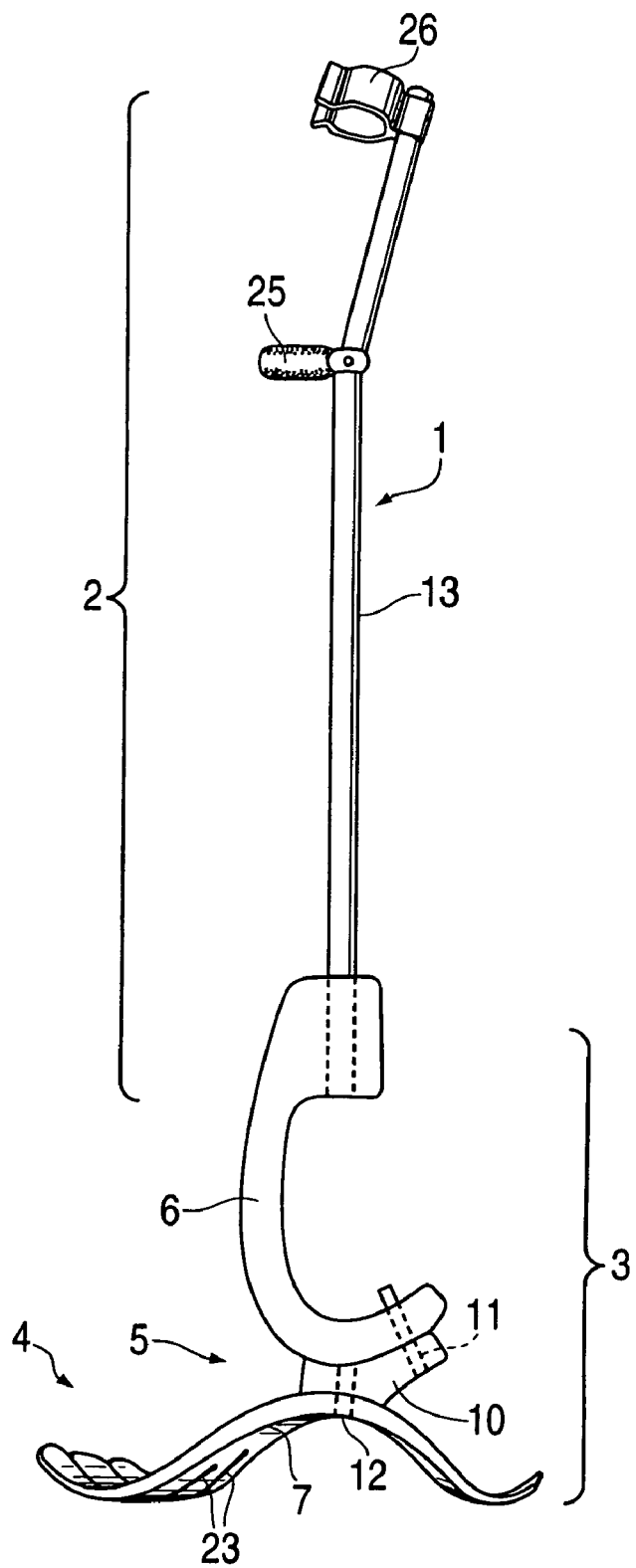
FIG. 1 is a left side view of a mobility assistance apparatus according to an embodiment of the invention.
Figure 2:
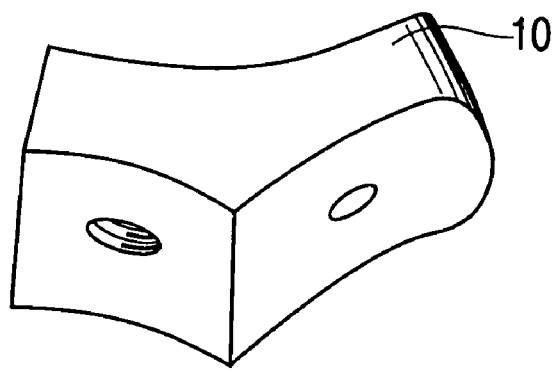
FIG. 2 is an enlarged view from below and to one side of a coupling element of the apparatus of FIG. 1 by which a foot keel and a shank of the apparatus are connected.
Figure 3:
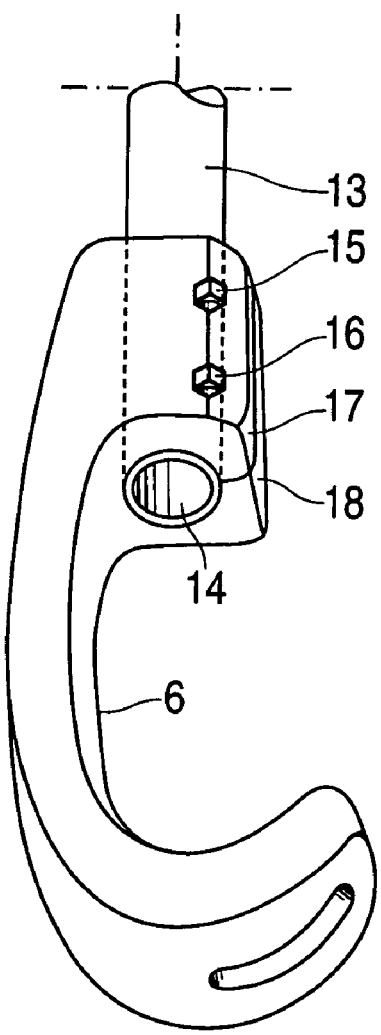
FIG. 3 is an enlarged left side view of a portion of the apparatus of FIG. 1 showing the connection between the lower end of a support member of the apparatus and the upper end of the shank.

Referring now to FIGS. 1-3 of the drawings, a mobility assistance apparatus 1 according to a preferred embodiment is formed of a walking aid 2 in the form of a forearm crutch and a device 3 connected to a lower portion of the walking aid for ground engagement. The device 3 has a dynamic response characteristic to forces associated with ambulating using the walking aid which generates forward propulsion to aid mobility. The device 3 in the embodiment is a resilient lower extremity prosthesis, e.g. a prosthetic foot, which stores energy during force loading and releases stored energy during force unloading to generate propulsive force. In the example embodiment the device 3 is a prosthesis according to commonly owned U.S. Pat. No. 6,562,075.

The prosthesis 3 includes a resilient foot 4, ankle 5 and calf shank 6. The foot 4 includes a foot keel 7 and optionally a protective covering not shown in FIG. 1 but like covering 8 shown in outline in FIG. 4, for example. The covering 8, which may be formed of rubber, has ridges 9 on the bottom, ground engaging surface thereof to resist slipping during use. If a separate protective covering is not employed on the device 3, ridges or other surface irregularities can be provided directly on the under surface of the foot keel to resist slippage as discussed below.

The shank 6 is connected to the foot keel by way of a coupling element 10 and fasteners 11 and 12 to form the ankle 5 of the prosthesis. At least a lower portion of the shank is anterior facing convexly curved. The foot keel is upwardly arched in its midportion. The adjacent radii of curvatures of the resilient foot keel and calf shank of the prosthesis create a dynamic response capability and motion outcome of the prosthesis in a direction having horizontal and vertical components as explained with reference to FIGS. 1 and 2 of U.S. Pat. No. 6,562,075, to generate a propulsive force during ambulating.

The walking aid 2 of the apparatus 1 is formed with a hollow staff 13 that serves as a support member capable of bearing vertical forces from the weight of the user on the crutch during use as a walking aid. A hand grip 25 and forearm support 26 are mounted on the staff. The length of the staff could be adjustable as by the use of adjustably telescoped staff portions, not shown. While the walking aid 2 in the mobility assistance apparatus 1 is a forearm crutch, other types of walking aids could be used as the walking aid in the apparatus, including another type of crutch, a cane, or a walker, for maximizing functionality and mobility, while lessening the user's necessary energy expenditure and discomfort associated therewith.

The device 3 is preferably capable of sagittal and transverse plane motion in response to forces associated with ambulating using the walking aid. Transverse plane motion, provided for example by the provision of longitudinally extending expansion joints 23 in the foot keel as disclosed in related U.S. Pat. No. 6,562,075 and/or by the use of a coupling element permitting motion of the foot about a joint axis which is at least primarily in the frontal and transverse planes as shown in FIGS. 28-35 of commonly owned related U.S. patent application Ser. No. 10/473,465, ensures, together with sagittal plane motion capability, that the bottom surface of the foot keel will remain parallel to the ground, maintaining maximum contact and traction throughout the ambulatory cycle. The energy storing prosthetic foot 3 is capable of enhancing and/or replicating the propulsion that an individual would experience at the foot, ankle, and calf during the gait cycle, if uninjured or able bodied.

Figure 4:
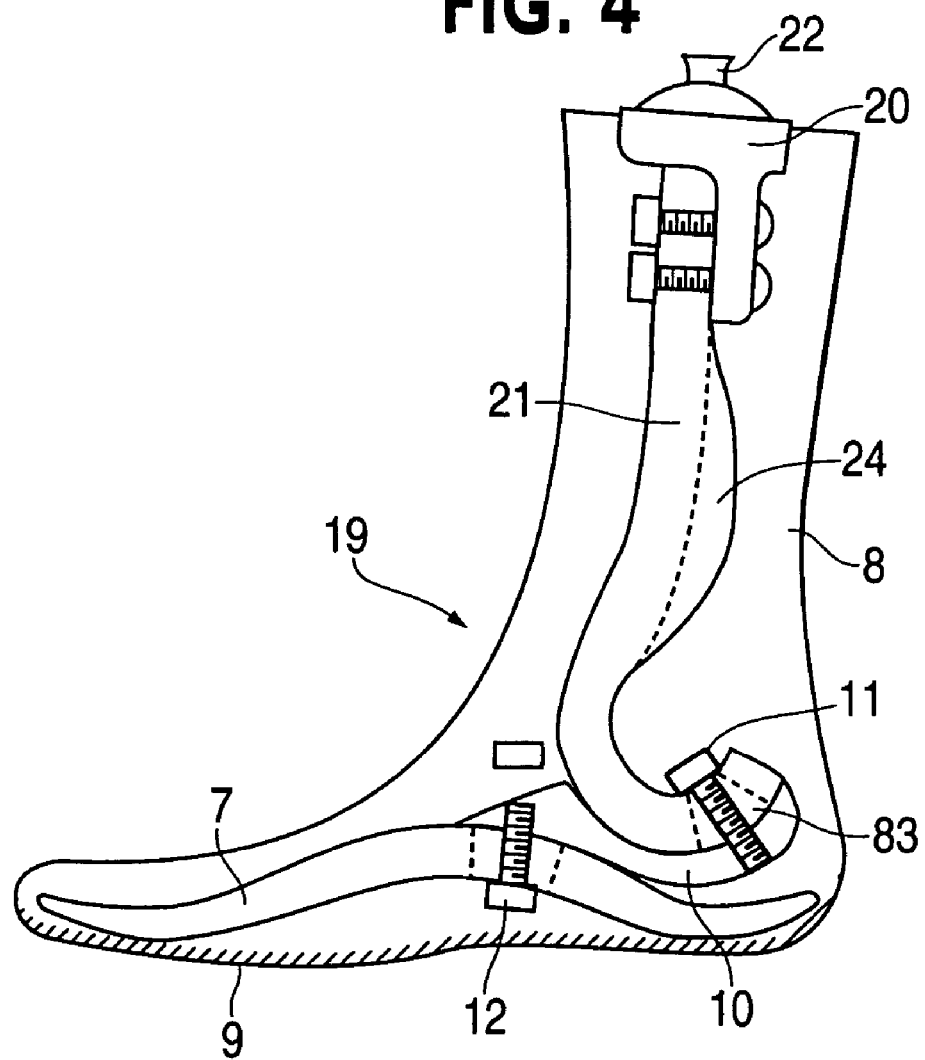
FIG. 4 is a left side view of another form of a resilient lower extremity prosthesis for use in the apparatus of FIG. 1, the prosthesis having an outer protective covering, shown in outline, the covering having a slip resistant lower surface for ground engagement, a male pyramid connector of a male/female pyramid connection system being shown for connecting the prosthesis to a lower end of a supporting member of the apparatus.

In the absence of a protective covering on the prosthesis 3 as shown in FIG. 4, a rubber surface or a compressible foam surface is preferably bonded to the underside of the foot keel 7 using an epoxy glue, for example. The rubber or foam surface is preferably provided with a slip resistant/traction characteristic. For example, corrugated vanes could be formed on the ground engaging rubber or foam surface for increased traction over wet surfaces. In addition, or alternatively, a boot which fits over the entire body of the prosthetic foot keel, excluding the shank, can be used to achieve variable traction needs, the bottom surface of the boot being provided with a slip resistant surface, e.g. cleats, ridges, etc.

The releasable connection between the lower end of staff 13 and the upper end of shank 6 in the apparatus 1 is shown in the enlarged view of FIG. 3. The upper end of the shank is formed with an elongated opening 14 for receiving the lower end of staff 13. Once received in the opening, the staff is securely clamped to the shank by tightening bolts 15 and 16 to draw the free side edges 17 and 18 of the shank along the opening together. This connection can be readily adjusted by loosening the bolts, telescoping the staff relative to the shank to the desired position and reclamping the staff in the adjusted position by tightening the bolts.

The connection between the prosthesis and the walking aid/support member is not limited to that shown in the example embodiment of FIGS. 1-3. Other types of connections including a conventional male/female pyramid system, for example, could be employed. The prosthetic foot 19 in FIG. 4, for use in a mobility assistance apparatus of the invention, has an adapter 20 bolted to the upper end of the shank 21. The adapter 20 has a male pyramid 22 thereon for reception in a complementarily shaped socket of an adapter provided on the lower end of staff 13.

The device 3 according to the invention may be formed from acetal homopolymer or copolymer (Delrin/Celcon), for example, or other materials including aluminum, carbon or graphite composites, glass, and/or Kevlar. In the preferred embodiment the device 3 is formed of acetal plastic, by either machining or injection molding.

The prosthetic foot 19 in FIG. 4 is similar to that in FIG. 1 although the shank 21 thereof is reversely curved on itself above an anterior convexly curved lower portion. Fins 24 are formed on the posterior side of the reversely curved portion of the shank to alter the flexing characteristic of the shank as discussed with respect to FIGS. 28-32 of commonly owned related U.S. patent application Ser. No. 10/473,680.

The device 3 of the invention is not limited to the two examples of FIGS. 1 and 4. Other devices, particularly lower extremity prostheses/prosthetic feet capable of storing and releasing energy during use to generate propulsion could be used in the mobility assistance apparatus and method of the invention for stabilizing the walking system and lessening the user's necessary expenditure of energy and discomfort associated therein. Examples of additional prosthesis for use in the mobility assistance apparatus of the invention are shown in FIGS. 5-13. These prostheses are relatively inexpensive in that they can be monolithically formed as by injection molding acetal plastic. The resulting mobility assistance apparatus employing the prosthesis is able to create power for enhancing mobility yet is low cost.

Figure 5:
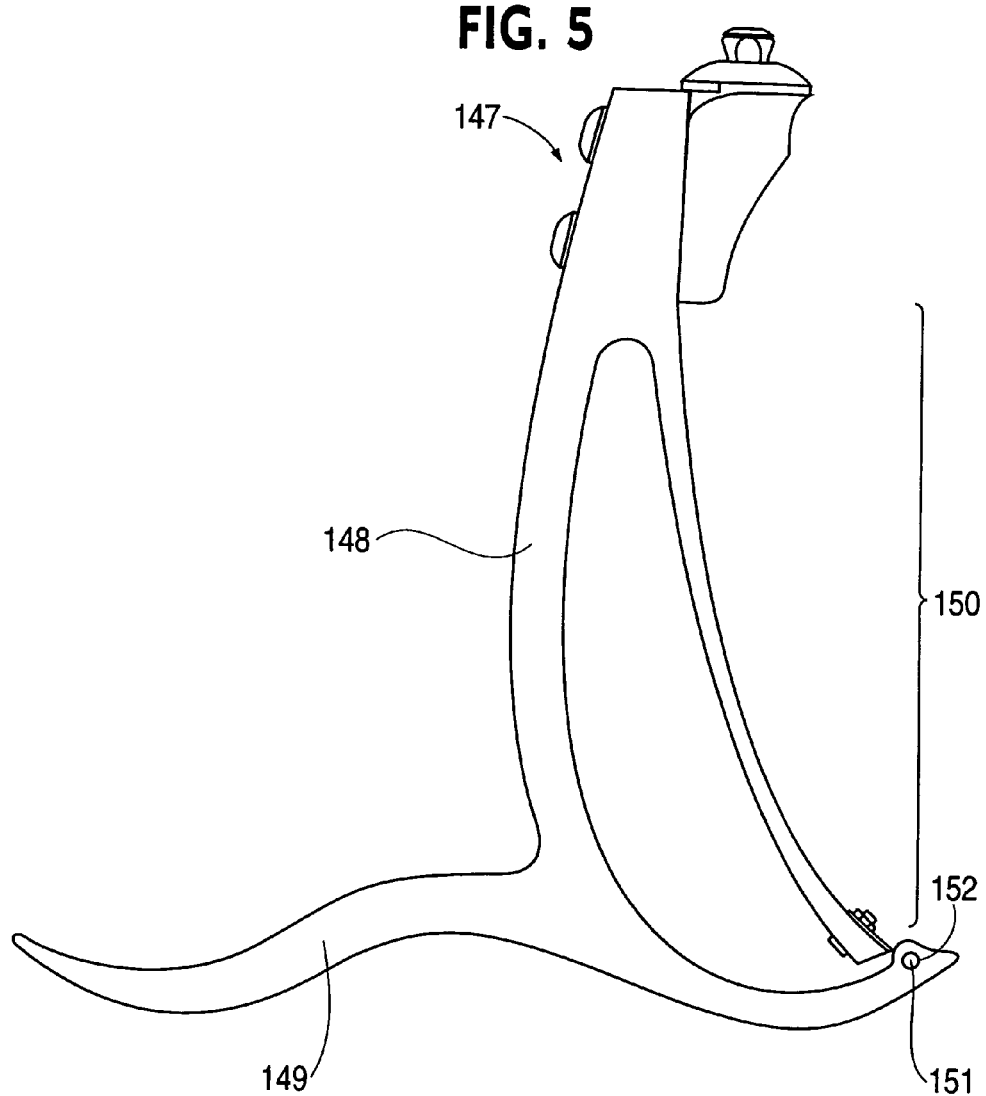
FIG. 5 is a side view of another embodiment of a prosthetic foot for use in the mobility assistance apparatus, wherein the calf shank and foot keel and also a posterior calf device of the prosthesis are monolithically formed, the distal end of a spring of the posterior calf device being pivotably connected to the posterior of the foot keel.
Figure 6:
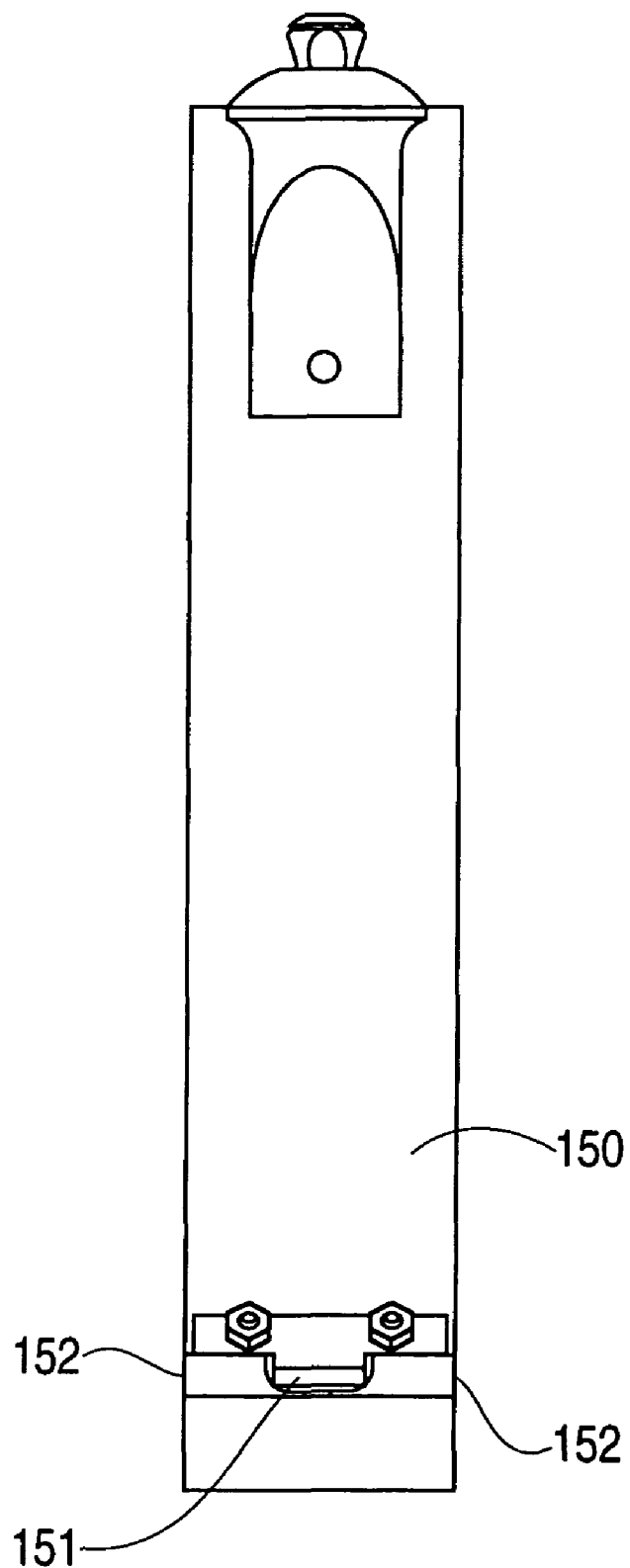
FIG. 6 is a rear view of the prosthesis of FIG. 5.
Figure 7:
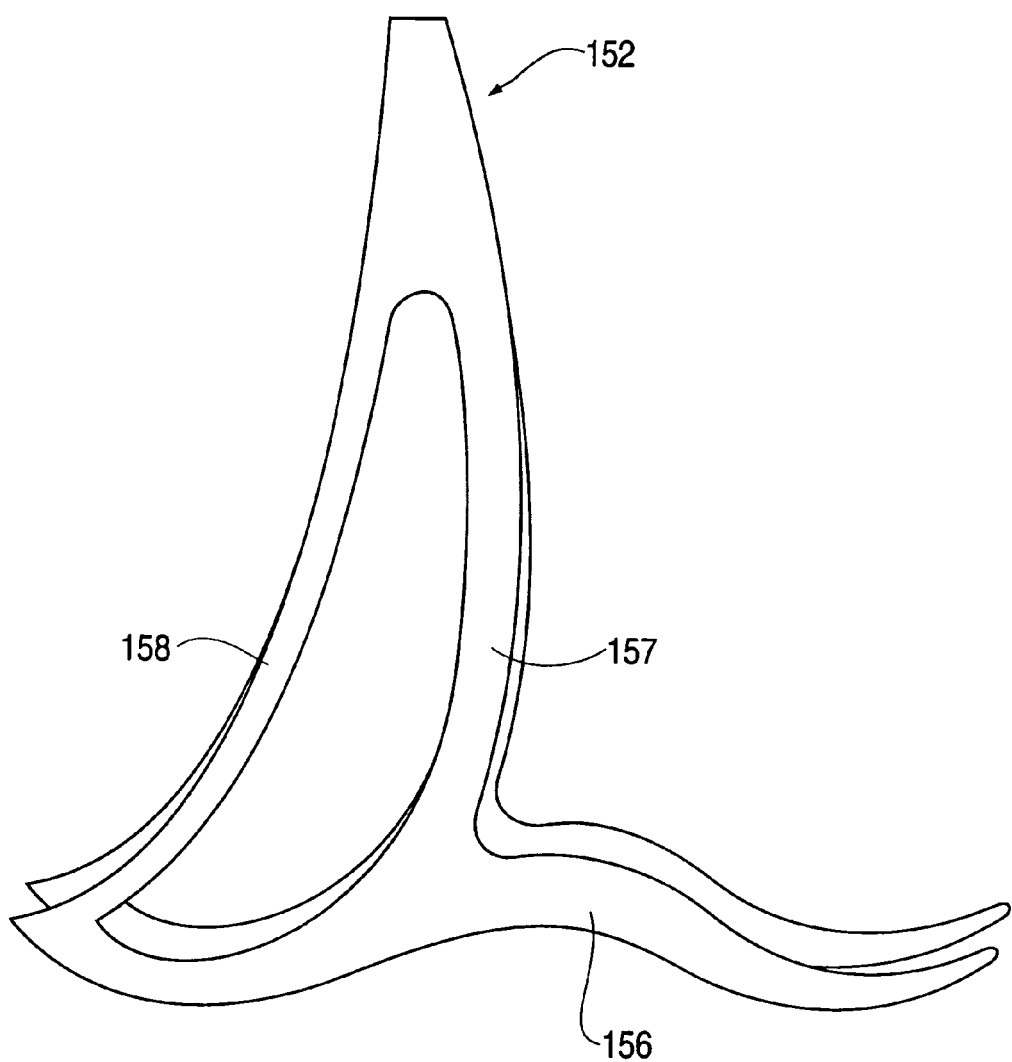
FIG. 7 is a side view of another example of a prosthetic foot similar to that of FIGS. 5 and 6 for use in the mobility assistance apparatus, but where the foot keel, calf shank and posterior calf device are monolithically formed with three, side by side longitudinal sections freely movable with respect to one another at their distal ends but connected at the proximal end of the calf shank, with the center section being wider, and at its distal surface higher, than the outer sections.
Figure 8:
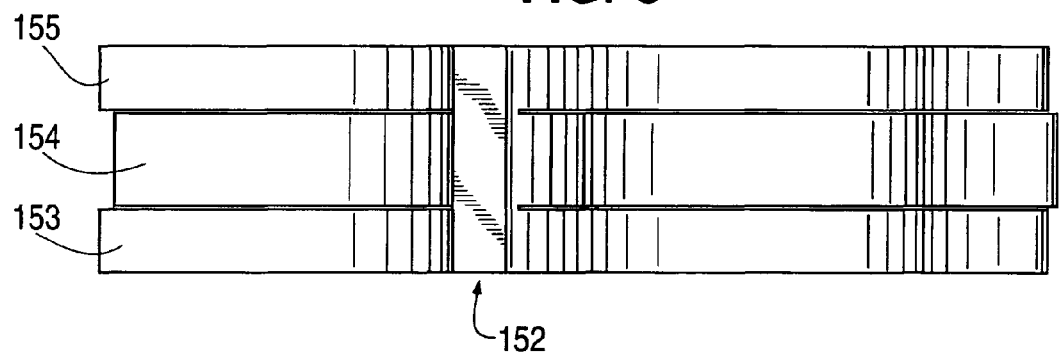
FIG. 8 is a top view of the prosthesis of FIG. 7.
Figure 9:
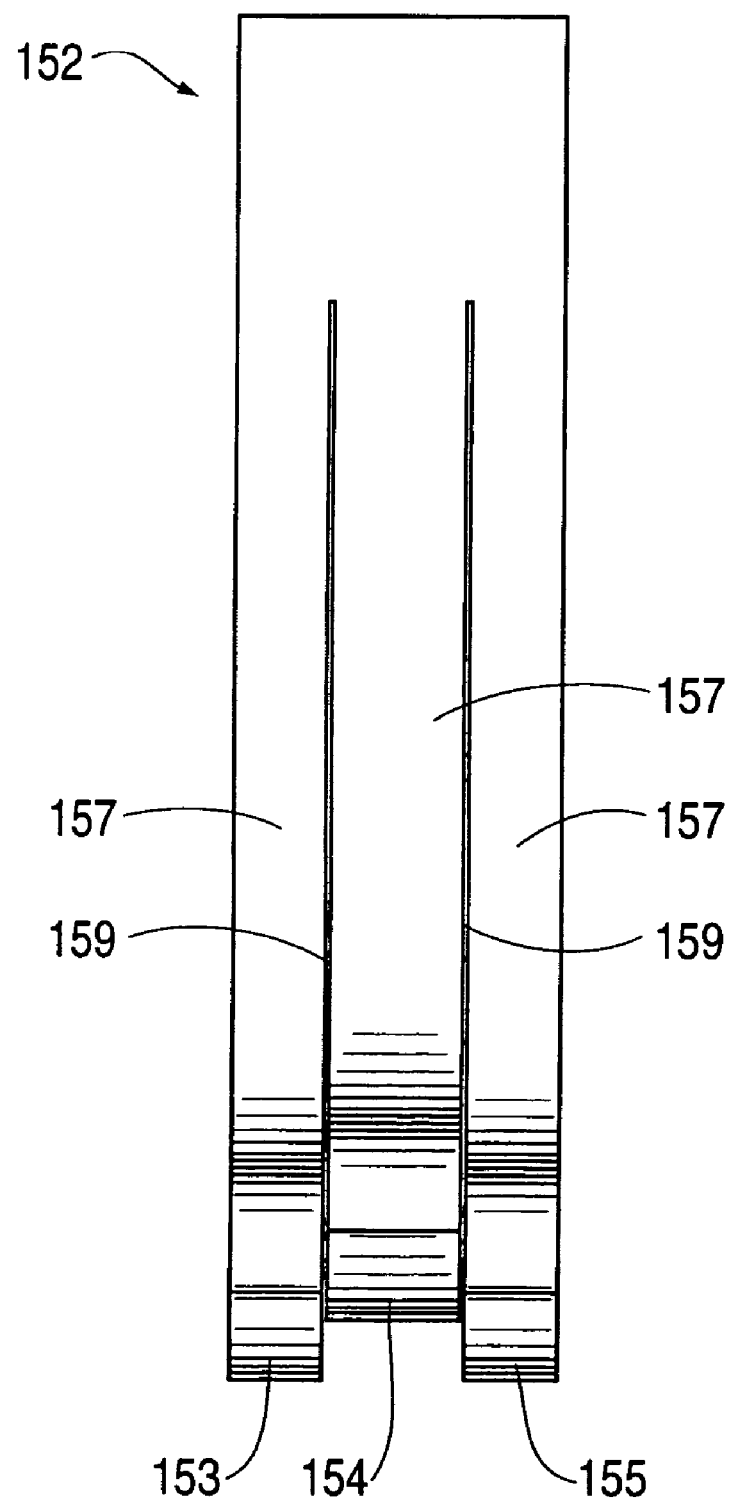
FIG. 9 is a front view of the prosthesis of FIGS. 7 and 8.
Figure 10:
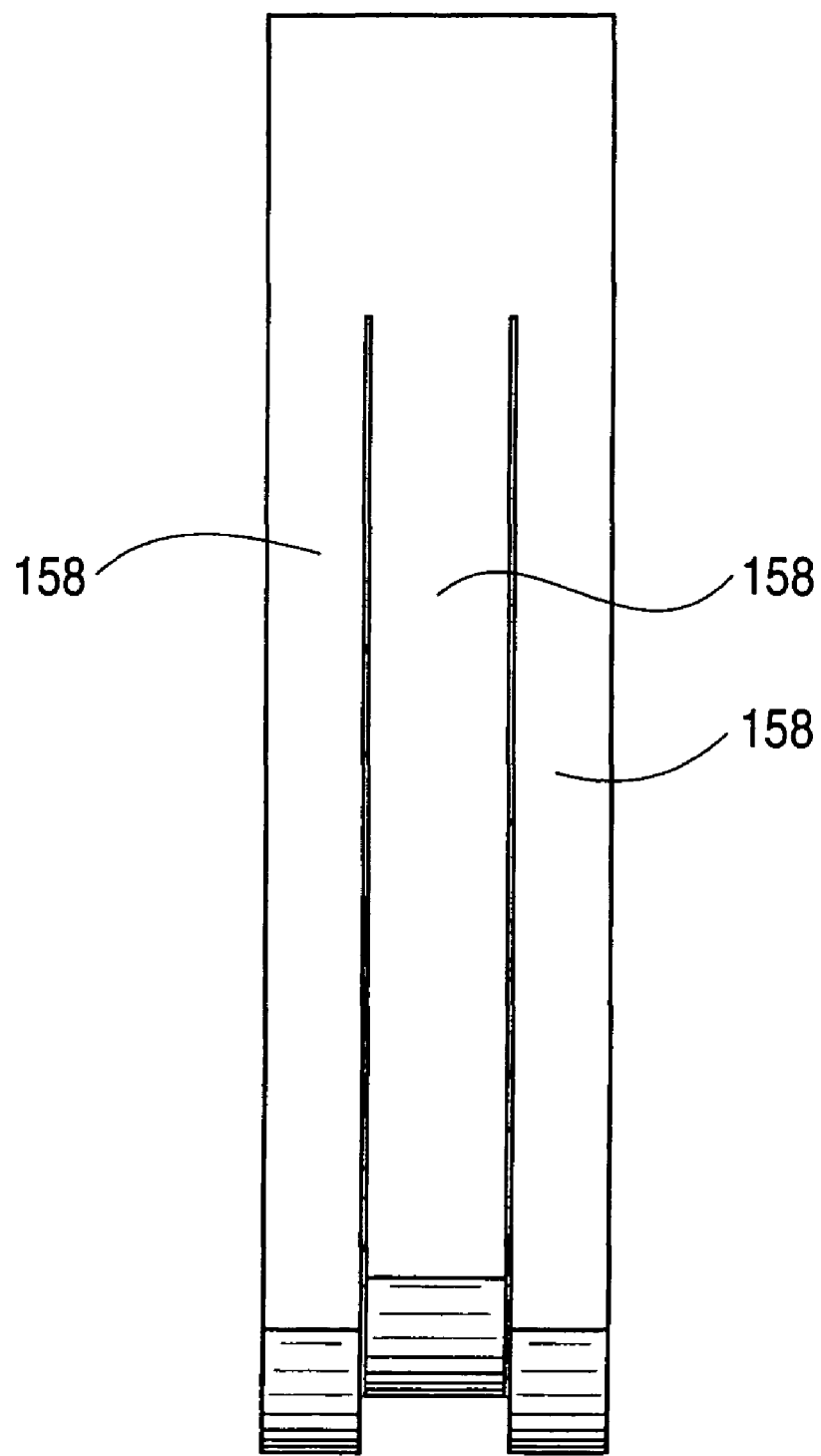
FIG. 10 is a rear view of the prosthesis of FIGS. 7-9.

The prosthetic foot 147 of FIGS. 5 and 6 is characterized by a calf shank 148, foot keel 149 and posterior calf device 150 which are monolithically formed. The calf shank 148 has an anterior facing convexly curved lower portion extending upwardly from the foot keel as in previously described prostheses. The posterior calf device 150 is in the form of an elongated, resilient, curved spring connected at its proximal end to an upper portion of the calf shank and at its distal end the spring is pivotably connected to a posterior portion of the foot keel by a bracket with pivot pin 151 mounted on the distal end of the spring with the pin extending through an aperture 152 in the posterior end of the foot keel. The ends of pins 151 are anchored in the openings 152 in the foot keel as shown in the drawings. With anterior or posterior motion of the upper end of the calf shank in gait with the mobility assistance apparatus of the invention, the concavity of the curved spring will be expanded or compressed to store energy within the motion limits of the spring. The stored energy will then be returned upon force unloading in gait to add to the kinetic power available for propulsive force of the user's body.

The prosthesis in FIGS. 7-10 is a prosthetic foot 152 having three longitudinal sections 153-155. Each longitudinal section is monolithically formed with a foot keel 156, calf shank 157 and posterior calf device 158. The sections 153-155 are movable independent of one another at their distal ends, where they are separated by gaps 159, but the sections are integral at their proximal ends, e.g. at the upper end of the calf shank. This integral construction can be provided by use of fasteners for connecting the proximal ends of the respective, separately formed longitudinal sections to one another. Alternatively, the resilient longitudinal sections can be monolithically formed with one another such that they are connected at their upper ends while freely movable relative to each other at their distal ends where gaps 159 separate the sections.

The center longitudinal section 154 in the prosthesis 152 is wider than the medial and lateral sections 153 and 155 and also, at its distal end, it is higher than the sections 153 and 155. This construction provides advantages in support on uneven or inclined surfaces as discussed previously in connection with the use of a plurality of longitudinal anterior and posterior foot keel struts separated by expansion joints. The number of the plurality of longitudinal sections employed in the prosthesis can be other than three and the relative widths of the sections can be varied from that shown in FIGS. 7-10. The distal ends of the curved spring of posterior calf device 158 of each longitudinal section is formed integrally with the hindfoot of its foot keel 156 rather than being pivotably connected thereto as in the embodiment of FIGS. 5 and 6. A suitable adapter, not shown, is connected to the upper end of the calf shank of the prosthesis 152 for connection with the support member, hollow shaft 13, of the walking aid 2 to form a mobility assistance apparatus of the invention as described in previous embodiments.

Figure 11:
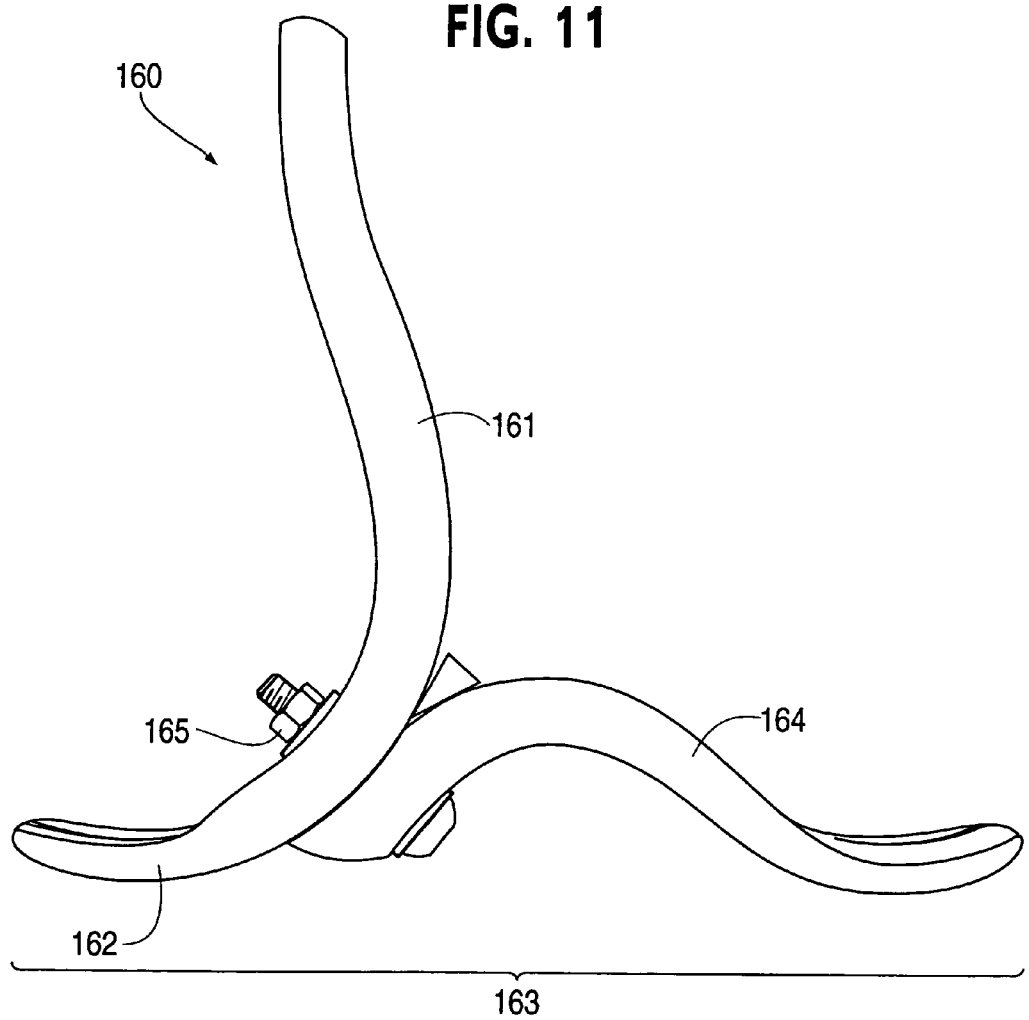
FIG. 11 is a side view of another form of the calf shank and foot keel of a prosthesis for the mobility assistance apparatus of the invention wherein the shank is monolithically formed with a posterior portion of the foot keel, which is connected by fasteners to a forefoot and midfoot forming member of the prosthesis.
Figure 12:
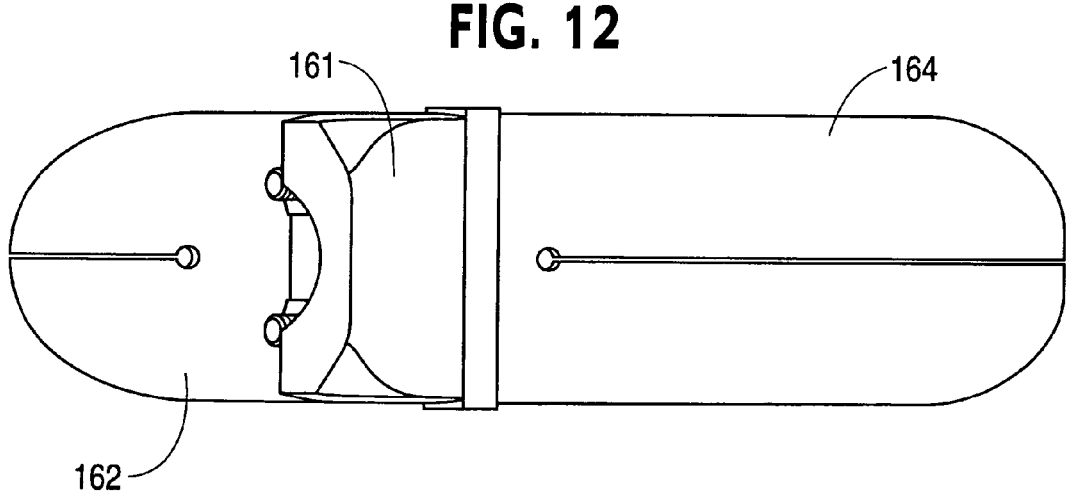
FIG. 12 is a top view of the calf shank and foot keel of FIG. 11.
Figure 13:
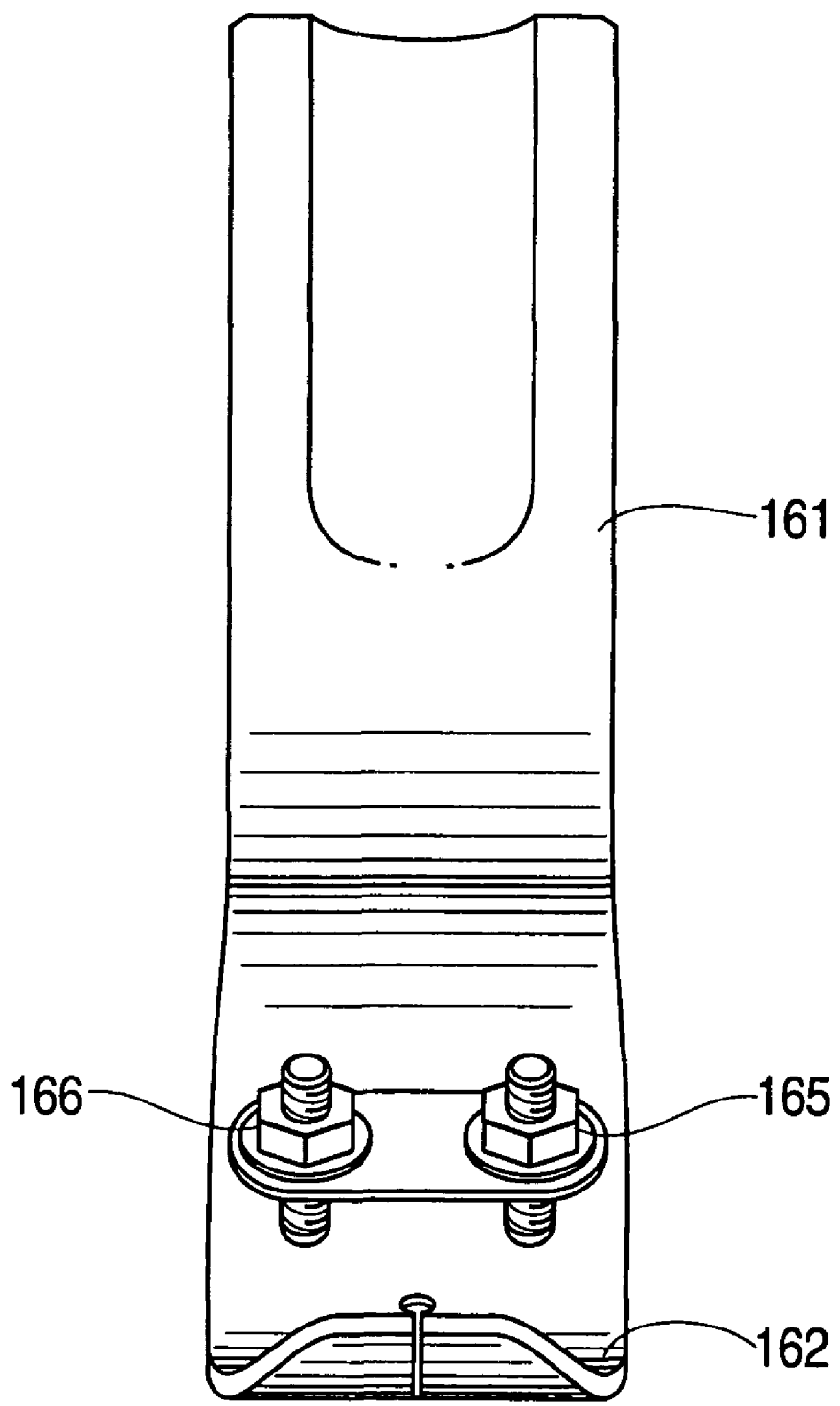
FIG. 13 is a rear view of the calf shank and foot keel of FIGS. 11 and 12.

Another form of construction for the prosthetic foot for use with the invention is illustrated in FIGS. 11-13 wherein the prosthetic foot 160 comprises a calf shank 161 monolithically formed with a posterior portion 162 and foot keel 163. The resilient member of the shank and hindfoot is connected to a resilient member 164 forming forefoot and midfoot portions of the foot keel by fasteners 165 and 166 as shown in the drawings. A posterior calf device, not shown in FIGS. 11-13, can be formed as part of the prosthesis as disclosed above. Likewise, an adapter for connection to a support member of a walking aid is to be attached to the upper end of the calf shank 161.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings, and the appended claims without departing from the spirit of the invention. In addition to variations and modifications in the component parts and/or arrangements, alternative uses will also be apparent to those skilled in the art.

We claim:

1. A mobility assistance apparatus comprising; in combination:
   a walking aid being selected from a group consisting of a crutch,
   a cane, and a walker; and
   a device connected to a lower portion of the walking aid for ground engagement, the device having a dynamic response characteristic to forces associated with ambulating using the walking aid which generates forward propulsion to aid mobility;
   wherein the device includes a resilient foot, an ankle and a shank which store energy during force loading and release stored energy during force unloading to generate propulsive force, the shank being generally rectangular in shape with a side to side width being greater than an anterior posterior thickness, the shank having a lower end which is anterior facing convexly curved, an elongated portion extending upward from the curved lower end, and a substantially curvilinear, substantially vertically oriented upper end, and wherein the curved lower end is coupled to the resilient foot, and the upper end is connected to the lower portion of the walking aid.

2. The mobility assistance apparatus according to claim 1, wherein the resilient foot includes a foot keel, the shank being connected to the foot keel to form the ankle.

3. The mobility assistance apparatus according to claim 1, wherein the device is monolithically formed.

4. The mobility assistance apparatus according to claim 1, wherein the device has a slip resistant lower surface for ground engagement.

5. The mobility assistance apparatus according to claim 1, wherein the walking aid is a crutch, and the device is connected to the lower portion of the crutch.

6. The mobility assistance apparatus according to claim 1, wherein the device is capable of sagittal and transverse plane motion in response to forces associated with ambulating using the walking aid.

7. The mobility assistance apparatus according to claim 1, further comprising a releasable connection connecting the device to the lower portion of the walking aid.

8. The mobility assistance apparatus according to claim 7, wherein the releasable connection is selected from the group consisting of a male/female pyramid system and an elongated opening at the upper end of the device which telescopingly receives the lower portion of the walking aid.

9. A mobility assistance apparatus comprising; in combination:
   a walking aid being selected from a group consisting of a crutch, a cane, and a walker; and
   a resilient prosthesis including a foot, an ankle and a shank connected to a lower portion of the walking aid for ground engagements;
   wherein the shank is generally rectangular in shape with a side to side width being greater than an anterior posterior thickness, the shank having a lower end which is anterior facing convexly curved, an elongated portion extending upward from the curved lower end, and a substantially curvilinear, substantially vertically oriented upper end, and wherein the curved lower end is coupled to the foot, and the upper end is connected to the lower portion of the walking aid.

10. The mobility assistance apparatus according to claim 9, wherein the resilient prosthesis stores and releases energy to aid mobility with ambulating using the walking aid.

11. The mobility assistance apparatus according to claim 9, wherein the resilient prosthesis has sagittal and transverse plane motion capability in response to forces associated with ambulating using the walking aid.

12. The mobility assistance apparatus according to claim 9, wherein the foot includes a foot keel, the shank being connected to the foot keel to form the ankle.

13. The mobility assistance apparatus according to claim 9, wherein the foot has a slip resistant lower surface for ground engagement.

14. The mobility assistance apparatus according to claim 9, wherein the walking aid is a crutch, the resilient prosthesis being connected to a lower end of the crutch.

15. The mobility assistance apparatus according to claim 9, wherein a releasable connection is provided between the shank and the lower portion of the walking aid to connect the prosthesis to the walking aid.

16. The mobility assistance apparatus according to claim 15, wherein the releasable connection is selected from the group consisting of a male/female pyramid system and an elongated opening at the upper end of the shank telescopingly receiving the lower portion of the walking aid.

17. The mobility assistance apparatus according to claim 9, wherein the resilient prosthesis further includes a resilient posterior calf device connected to an upper portion of the shank and a lower portion of the prosthesis, the device flexing to store energy during force loading of the apparatus and return the stored energy during force unloading.

18. The mobility assistance apparatus according to claim 17, wherein the shank and the posterior calf device are monolithically formed.

19. The mobility assistance apparatus according to claim 18, wherein the foot and ankle are also monolithically formed with the shank and the posterior calf device.

20. A method of improving the mobility of a person using a walking aid, comprising:
   providing a walking aid being selected from a group consisting of a cane, a crutch and a walker
   providing a device having a dynamic response characteristic to forces associated with ambulating using the walking aid which generates forward propulsion to aid mobility;
   connecting the device to a lower portion of the walking aid for ground engagement with ambulating using the walking aid;
   wherein the device includes a resilient foot, an ankle and a shank which store energy during force loading and release stored energy during force unloading to generate propulsive force, the shank being generally rectangular in shape with a side to side width being greater than an anterior posterior thickness, the shank having a lower end which is anterior facing convexly curved being connected to the resilient foot, an elongated portion extending upward from the curved lower end, and a substantially curvilinear, substantially vertically oriented upper end, and wherein the curved lower end is coupled to the resilient foot, and the upper end is connected to the lower portion of the walking aid.

21. The method of claim 20, wherein the device is a lower extremity prosthesis.

22. The method of claim 21, wherein the connecting includes connecting the upper end of the shank to a lower end of the walking aid.

23. A mobility assistance apparatus comprising:
a walking aid being selected from a group consisting of a cane, a crutch and a walker, the walking aid having a support member capable of bearing vertical forces during use of the walking aid;
a device connected to a lower portion of the support member for ground engagement, the device having a dynamic response characteristic to forces associated with ambulating using the walking aid which generates forward propulsion to aid mobility;
wherein the device includes a resilient foot, an ankle and a shank which store energy during force loading and release stored energy during force unloading to generate propulsive force, the shank being generally rectangular in shape with a side to side width being greater than an anterior posterior thickness, the shank having a lower end which is anterior facing convexly curved, an elongated portion extending upward from the curved lower end, and a substantially curvilinear, substantially vertically oriented upper end, and wherein the curved lower end is coupled to the resilient foot, and the upper end is connected to the lower portion of the walking aid.

24. A mobility assistance apparatus comprising:
a walking aid being selected from a group consisting of a cane, a crutch and a walker, the walking aid having a support member capable of bearing vertical forces during use of the walking aid;
a resilient prosthesis including a foot, an ankle and a shank connected to a lower portion of the support member for ground engagement;
wherein the shank is generally rectangular in shape with a side to side width being greater than an anterior posterior thickness, the shank having a lower end which is anterior facing convexly curved, an elongated portion extending upward from the curved lower end, and a substantially curvilinear, substantially vertically oriented upper end, and wherein the curved lower end is coupled to the foot, and the upper end is connected to the lower portion of the support member.

* * * * *